(12) United States Patent
Di Fabrizio et al.

(10) Patent No.: US 10,343,164 B2
(45) Date of Patent: Jul. 9, 2019

(54) MICROFLUIDIC DEVICE THAT SEPARATES CELLS

(71) Applicant: KING ABDULLAH UNIVERSITY OF SCIENCE AND TECHNOLOGY, Thuwal (SA)

(72) Inventors: Enzo Di Fabrizio, Thuwal (SA); Gerardo Perozziello, Catanzaro (IT); Francesca Pardeo, Catanzaro (IT); Patrizio Candaloro, Catanzaro (IT)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 217 days.

(21) Appl. No.: 15/308,039

(22) PCT Filed: May 1, 2015

(86) PCT No.: PCT/IB2015/001595
§ 371 (c)(1),
(2) Date: Oct. 31, 2016

(87) PCT Pub. No.: WO2015/177654
PCT Pub. Date: Nov. 26, 2015

(65) Prior Publication Data
US 2017/0080424 A1    Mar. 23, 2017

Related U.S. Application Data

(60) Provisional application No. 61/987,459, filed on May 1, 2014.

(51) Int. Cl.
*B01D 63/08* (2006.01)
*B01D 61/18* (2006.01)
(Continued)

(52) U.S. Cl.
CPC ........ *B01L 3/502761* (2013.01); *B01D 61/18* (2013.01); *B01D 63/088* (2013.01); *B01L 3/502707* (2013.01); *B01L 3/502715* (2013.01); *B01L 3/502753* (2013.01); *G01N 1/4077* (2013.01); *G01N 15/1056* (2013.01); *B01L 2200/0652* (2013.01); *B01L 2300/0681* (2013.01); *B01L 2300/087* (2013.01); *B01L 2300/0816* (2013.01);
(Continued)

(58) Field of Classification Search
None
See application file for complete search history.

(56) References Cited

U.S. PATENT DOCUMENTS 7,964,078 B2   6/2011  Lee
8,304,230 B2   11/2012 Toner
(Continued)

OTHER PUBLICATIONS

International Search Report and Written Opinion of the International Searching Authority, dated Jan. 12, 2016 issued in International Application No. PCT/IB2015/001595.
(Continued)

*Primary Examiner* — Paul S Hyun
(74) *Attorney, Agent, or Firm* — Patent Portfolio Builders PLLC

(57) ABSTRACT

Devices and methods for separating cells include a membrane that allows cells to pass from a first chamber to a second chamber.

20 Claims, 11 Drawing Sheets

(51) Int. Cl.
 *G01N 1/40*    (2006.01)
 *B01L 3/00*    (2006.01)
 *G01N 15/10*    (2006.01)
 *G01N 15/00*    (2006.01)

(52) U.S. Cl.
 CPC ............... *B01L 2300/0887* (2013.01); *B01L 2400/0478* (2013.01); *G01N 2001/4088* (2013.01); *G01N 2015/0065* (2013.01); *G01N 2015/1006* (2013.01); *G01N 2015/1081* (2013.01)

(56) References Cited

U.S. PATENT DOCUMENTS

| | | |
|---|---|---|
| 8,372,579 B2 | 2/2013 | Toner |
| 8,703,457 B2 | 4/2014 | Yasuda |
| 8,815,092 B2 | 8/2014 | Zheng |
| 8,845,984 B2 | 9/2014 | Amshey |
| 8,895,298 B2 | 11/2014 | Toner |
| 8,986,966 B2 | 3/2015 | Toner |
| 9,109,197 B2 | 8/2015 | Yasuda |
| 9,174,222 B2 | 11/2015 | Huang |
| 9,370,732 B2 | 6/2016 | Gjerde |
| 9,416,776 B2 | 8/2016 | Ledden |
| 9,517,474 B2 | 12/2016 | Mao |
| 9,637,719 B2 | 5/2017 | Gjerde |
| 2002/0127565 A1* | 9/2002 | Cunningham ........ B01L 3/5085 435/6.19 |
| 2003/0198576 A1* | 10/2003 | Coyne ................... B01F 5/0646 422/400 |
| 2005/0148064 A1* | 7/2005 | Yamakawa ....... B01L 3/502753 435/287.2 |
| 2007/0296105 A1* | 12/2007 | Krause ................... B01D 61/00 264/48 |
| 2011/0244443 A1* | 10/2011 | van Rijn ............. A61M 1/3633 435/2 |
| 2012/0028349 A1 | 2/2012 | Giorgini et al. |
| 2014/0008210 A1 | 1/2014 | Guia et al. |
| 2014/0028349 A1 | 1/2014 | Savran et al. |

OTHER PUBLICATIONS

Xu, T., et al., Cancer Res. 2010, 70 (16), 6420-6.

\* cited by examiner

MICROFLUIDIC DEVICE THAT SEPARATES CELLS

PRIORITY CLAIM

This application is a U.S. national phase under 35 U.S.C. 371 of International Patent Application No. PCT/IB2015/001595, titled "A MICROFLUIDIC DEVICE THAT SEPARATES CELLS" and filed May 1, 2015, which application claims priority to U.S. Provisional Application No. 61/987,459, filed May 1, 2014, the full disclosures of which are hereby incorporated by reference in their entireties.

TECHNICAL FIELD

The invention features devices and methods for separating cells.

BACKGROUND

Separating components of biological fluids and tissues is often necessary for clinical diagnostic procedures, scientific research, and occasionally treatment of patients. In the clinical diagnostics field, for example, there is a need for devices and methods which permit rapid isolation of purified blood cells of a certain type for tests and procedures. Basic research also requires purified cell types from blood. Separation and purification might be effected in different ways.

SUMMARY

In one aspect, a device for sorting cells comprising a microfluidic device can include a top layer including an inlet and an outlet, a bottom layer including an inlet and an outlet, and a membrane between the top layer and the bottom layer, wherein a first chamber is between the top layer and the membrane, wherein a second chamber is between the membrane and the bottom layer, wherein the membrane separates the first chamber and the second chamber, and wherein the membrane has a filter that allow cells to pass from the first chamber to the second chamber.

In certain embodiments, the membrane can include antibodies. The membrane can include a poly(methyl methacrylate), a polycarbonate, a fluoropolymer, topas (cyclic olefin copolymer—COC), a silicone, a polystyrene, or a combination thereof.

In certain embodiments, at least one of the top layer and the bottom layer can include a polycarbonate, a fluoropolymer, topas (cyclic olefin copolymer—COC), a silicone, a polystyrene, or a combination thereof.

In certain embodiments, the filter can include a plurality of rectangular openings. The filter can include a plurality of circular openings. The filter can include a plurality of cross-shaped openings.

In certain embodiments, the membrane can have a thickness of between 2 and 100 micrometers. The device can have a thickness of between 0.2 to 2 millimeters.

In certain embodiments, the cells can include at least one of a tumor cell, a white blood cell, or a red blood cell.

In another aspect, a method of separating a plurality of categories of cells in a sample can include adding a sample including a plurality of categories of cells into an inlet of a microfluidic device, passing some but not all cells through a membrane in the microfluidic device, and collecting two output streams from at least two outlets from the microfluidic device, each output stream including cells of different categories. Adding cells can include injecting cells or pumping cells into the inlet.

Other aspects, embodiments, and features will be apparent from the following description, the drawings, and the claims.

DETAILED DESCRIPTION

A microfluidic device can be used for ultrapurification of biological samples. The sample can include a plurality of categories of cells. In particular, a microfluidic device can be used to sort cell categories by morphological and or bioaffinity differences. In some embodiments, one category of cells passes from a top layer of the microfluidic device to a bottom layer of the microfluidic device. In some embodiments, all but one category of cells passes from the top layer to the bottom layer. Sample preparation and separation can be a necessary step for many genetic, biochemical, and biological analyses of biological and environmental samples. See for example, U.S. patent application Ser. No. 13/122,169; T. Xu, et al., Cancer Res. 2010, 70 (16), 6420-6; W. Chen, et al., Adv. Healthc. Mater. 2013, each of which is incorporated by reference in its entirety.

A microfluidic device can be made of poly(methyl methacrylate) (PMMA), polycarbonate, teflon, topas (cyclic olefin copolymer—COC), silicone, polystyrene, a combination of them, and other polymers. The microfluidic device can be prepared by using micromilling, photolithography or alternatively by hot embossing or injection molding and solvent or UV assisted bonding. It can consist in an upper and a bottom chamber separated by an engineered filter membrane and connected to inlets and outlets. The membrane can integrate microholes of specific shape (rectangles, circles, cross, triangles). Once the biological sample containing different categories of cells is injected in the chip, the cells can be sorted exploiting the different dimensions of the cells because only some type of cells can pass through the microholes of the membrane. The cells are forced towards the holes of the membrane by gravity and/or by specific microfluidic protocols. The injection and handling of the samples into the device can be performed by external pipettes and/or external pumps and valves.

Figure 1:
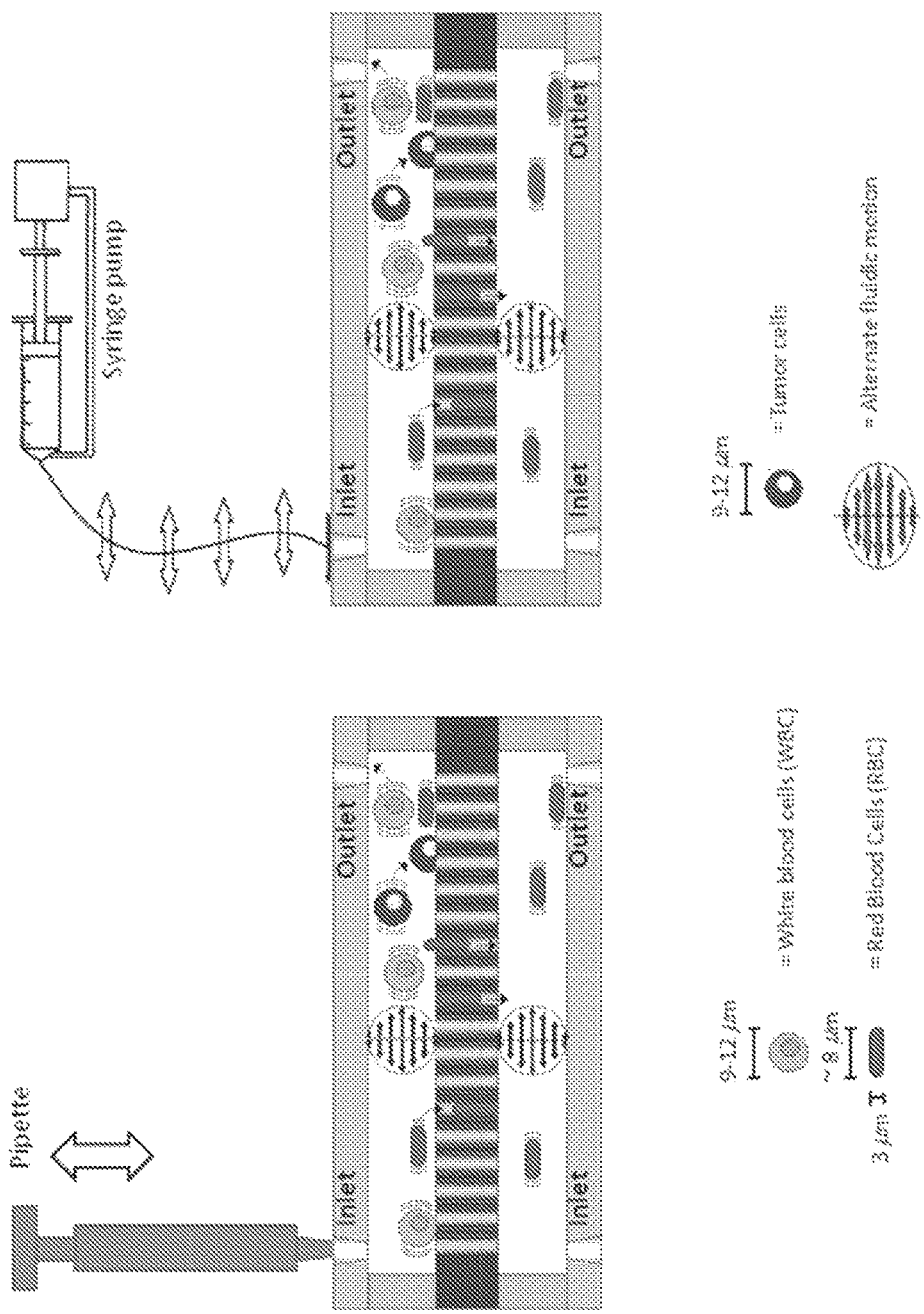
FIG. 1 is a schematic representation of the working principle of the microfluidic device.

Moreover, by means of biofunctionalization protocols, it is possible to bind specific antibodies to the membrane surface to sort by bioaffinity specific categories of cells (e.g. tumor cells). The device can be used to sort red blood cells, white blood cells, tumor cells, plasma and debris from blood. FIG. 1 is a schematic representation of a device working principle.

EXAMPLE

Device Fabrication

Figure 2:
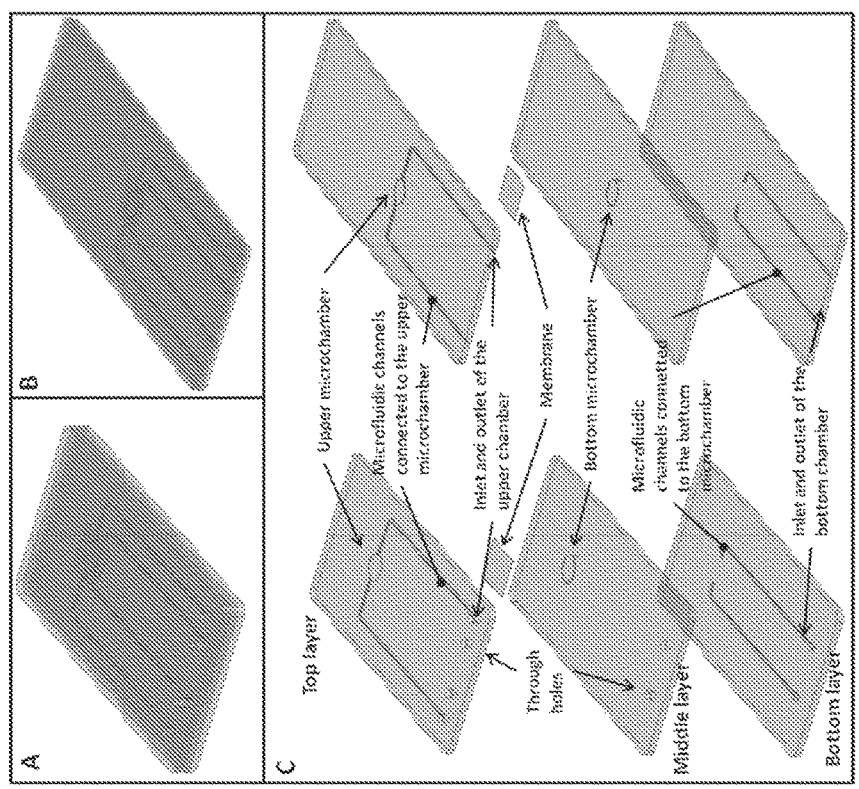
FIG. 2A and FIG. 2B show isometric view of the microfluidic device in two different configurations: inlets and outlets from the top (A), inlets and outlets from the side (B)
FIG. 2C is an exploded view of the two configurations of the microfluidic device. Other configurations can have inlets and outlets on both sides.

A microfluidic device composed of microfluidic chambers, channels, and membranes can be fabricated in PMMA by means of micromilling, photolithography and selective bonding techniques. The device fabrication can include the following phases: 1) membrane fabrication; 2) fabrication of the PMMA layers composing the microfluidic device; 3) assembly of the different pieces and selective bonding; 4) device biofunctionalization. FIG. 2 shows configurations of a microfluidic device.

Membrane Fabrication

Figure 3:
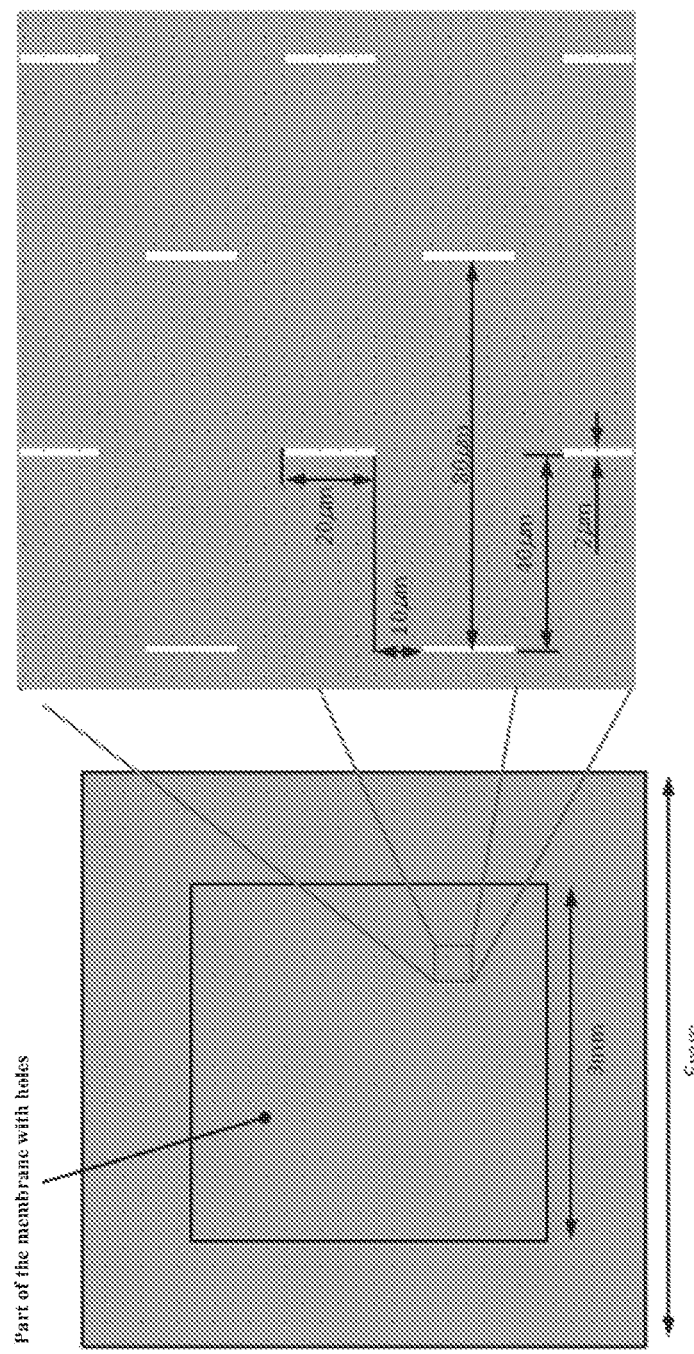
FIG. 3 shows a scheme of the filtering membrane.
Figure 4:
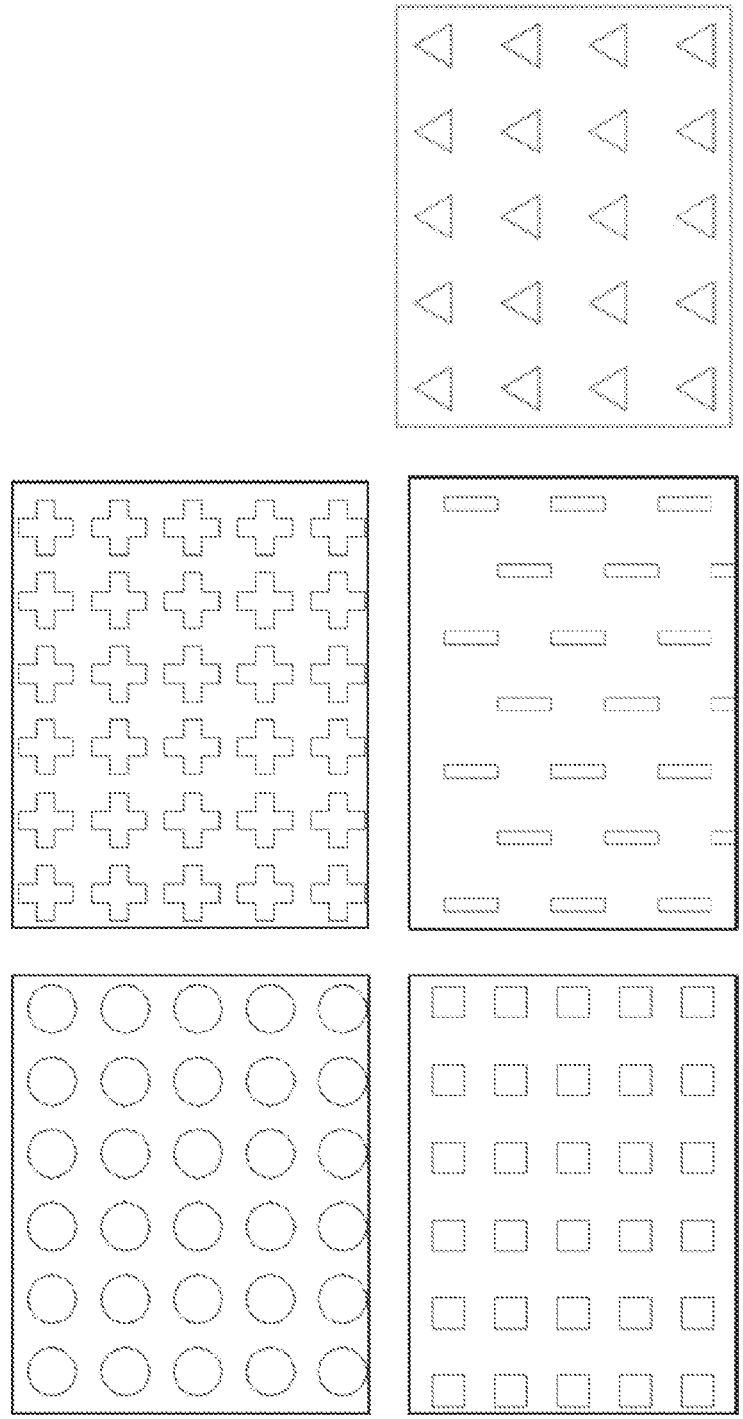
FIG. 4 shows different patterns for the filtering membranes.

The membrane can integrate engineered holes for filtering cells by morphological changes. In particular the membrane can be designed with rectangular holes. FIG. 3 shows a design of a membrane having specific dimension of the holes. The membrane holes can have different shapes like those showed in FIG. 4.

A membrane dimension of 5 mm×5 mm can ensure mechanical stability when integrated in the microfluidic device. The part of the membrane which integrates the holes is within an area of 3 mm×3 mm. The distance between the holes can be in a range of 0.01-0.04 mm, with consecutives columns which have an offset in the range of 0-0.03 mm in the vertical direction. The membrane thickness is of 0.01 mm which allows correct fabrication of the holes. The membrane is fabricated in polymethilmetacrylate (PMMA). The thickness of the membrane can be between 2 and 100 micrometers; the thickness of the membrane can be between 10 and 50 micrometers; the thickness of the membrane can be 10 micrometers.

The membrane can be fabricated by optical lithography. Liquid PMMA is deposited on a Silicon (Si) wafer, and it is heated up on a hot plate. Following a gold layer (Au) is sputtered on top of the PMMA. On this, a layer of photoresist (S1813) is deposited. By means of a photolithographic technique and the use of a chromium-glass optical mask, the hole patterns are transferred on the photoresist layer. Following the gold and the PMMA are selectively etched to realize the microholes on the PMMA membrane.

Figure 5:
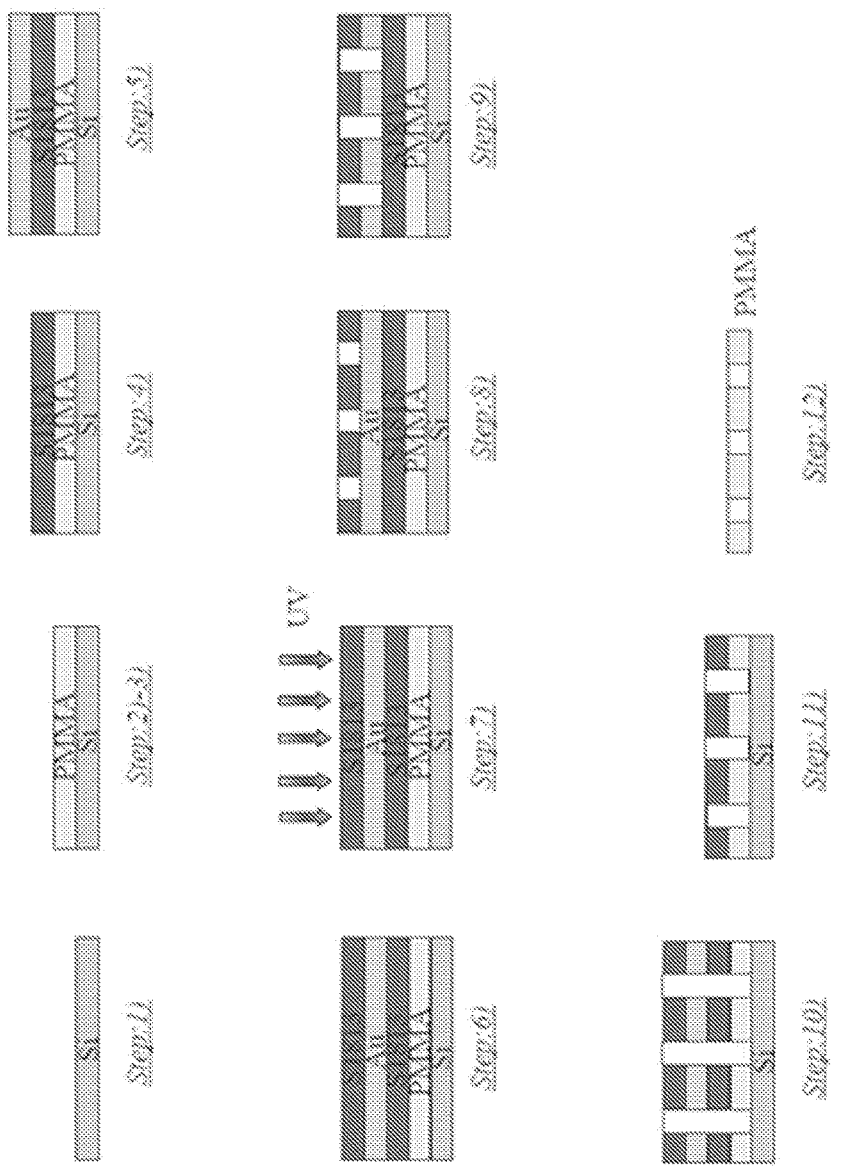
FIG. 5 shows fabrication steps of the PMMA filtering membrane.

FIG. 5 shows fabrication steps: step 1) Si wafer cleaning; step 2) Liquid PMMA preparation dissolving solid PMMA (30% wt) pellets in Anisole; step 3) PMMA spinning on the silicon wafer at 2000 rpm for 60 s, obtaining a layer of PMMA 0.01 mm thick and baking at 180° C. for 2 min; step 4) S1813 spinning on PMMA at 4000 rpm for 60 s, obtaining a layer of photoresist 0.001 mm thick; step 5) Au sputtering for 8 min to obtain a thickness of gold 0.0005-0.001 mm thick; step 6) S1813 spinning on PMMA at 4000 rpm for 60 s, obtaining a layer of photoresist 0.001 mm thick; step 7) Baking of the sample at 95° C. for 5 minutes and UV exposure under the optical mask for 12 seconds; step 8) S1813 development in the developer MF322 or MF319 for 1 min and rinsing in DI water for 1 min.; step 9) Au etching in KI:I2:H$_2$O (100 g:25 g:500 g) for 1 min and rinsing in DI water for 1 min; step 10) PMMA selective etching by a deep reactive ion etching (DRIE) instrument (parameters: Gas: O2, Flow=15 sccm; Ar, Flow=30 sccm, Power to coil=200 W, Power to Platen=50 W); step 11) Au removal by putting the sample in KI:I2:H$_2$O (100 g:25 g:500 g) for 1 min and rinsing in DI water for 1 min; step 12) PMMA membrane detachment from the silicon wafer by immersing it in Isopropanol for 1 h.

Figure 6:
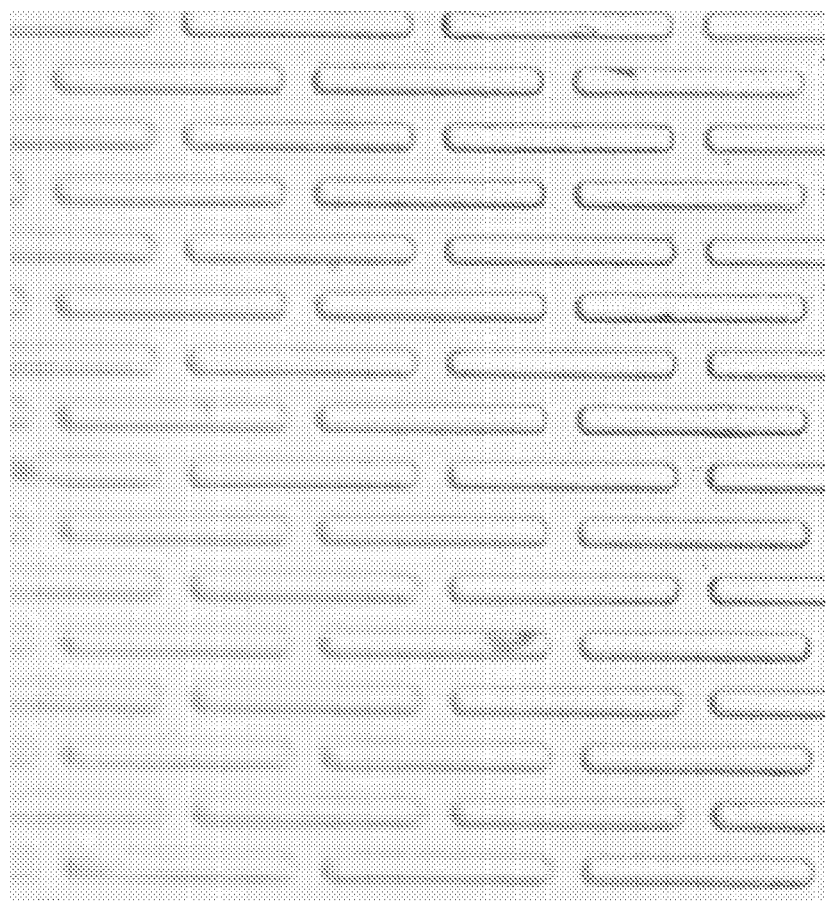
FIG. 6 shows a PMMA membrane having holes of rectangular shape.
Figure 7:
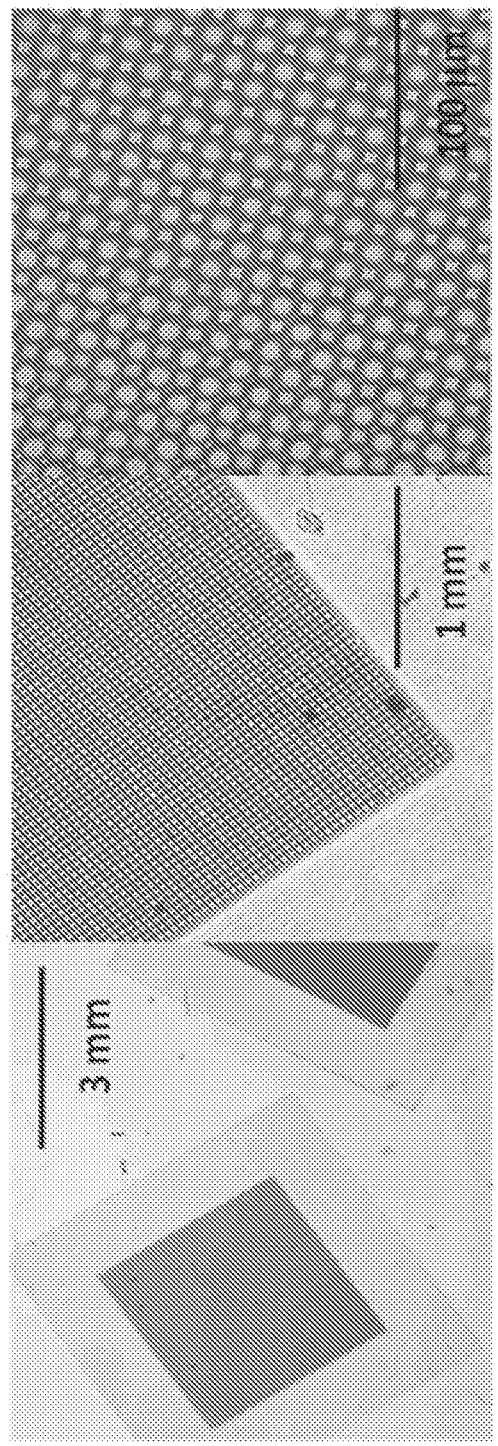
FIG. 7 shows membranes with circular holes.

FIG. 6 shows a PMMA membrane having holes of rectangular shape (width 0.055 mm). In FIG. 7, membranes are with circular holes.

PMMA Layers

The device can include 3 layers of PMMA of thickness which can be, for each layer, in a range of 0.5-1 mm. These can be machined by micromilling to obtain microchambers of 3 mm×3 mm side (this dimension is constrained by the dimension of the membrane if the membrane will be fabricated bigger then the dimension of this chamber must be adjusted accordingly) and 0.1 mm depth with conical inlet and outlet, connected to microchannels (0.25-0.5 mm wide and 0.1-0.25 mm deep) which are connected with the outside. Two holes in these layers in the range of 1-3 mm are also fabricated which are used as alignment holes during the assembly.

The different layers are fabricated by micromilling using tools having diameter of 0.25, 0.5 and 1 mm in diameter and a rotational speed of 8000 and 10000 rpm. It can be used a feed rate of 80 mm/min and a cutting depth of 0.1 and 0.25 mm.

Microfluidic Chambers Assembly

The PMMA layers and the membranes can bond together to create a single piece which integrate the microfluidic chamber.

The bonding process can be a UV or solvent assisted bonding. These two processes can include placing the PMMA layers under UV (for 70-140 seconds) or in ethanol (for 15-20 minutes). After this, the PMMA layers and the membrane can be assembled together, pressed (at 5-15 kN) at a temperature of 45° C. in case of the ethanol was used or 85° C. in case the UV was used for 1 to 2 hours.

Figure 8:
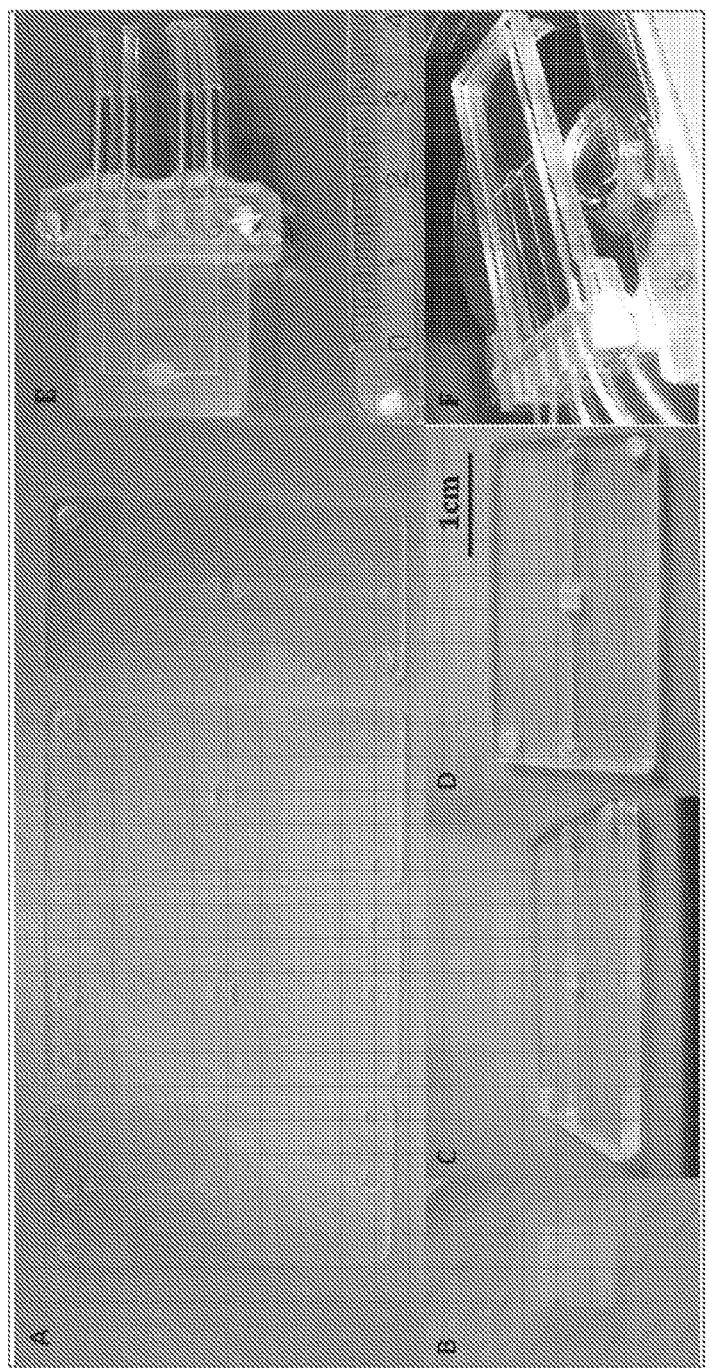
FIG. 8A shows layers of the microfluidic device.
FIG. 8B shows a filtering membrane (5 mm side)
FIG. 8C shows isometric view of the assembled microfluidic device.
FIG. 8D shows a top view of the assembled microfluidic device.
FIG. 8E is a view of a layout of the microfluidic device having inlets and outlets on the same side and connected to external tubes by a polymer frame integrating gaskets.
FIG. 8F shows another configuration of the device having inlets and outlets from the side.

FIG. 8 shows real pictures of different device configurations.

Microfluidic Device Biofunctionalization

By means of biofunctionalization, it is possible to bind specific antibodies on the membrane surface to isolate particular cell types by bioaffinity. For instance, tumor cells can be isolated by binding anti-EPCAM biotinylated antibodies. The biofunctionlization can be done on an assembled microfluidic device by injecting different reagents and biomolecules in the upper microfluidic chamber.

The biofunctionlization can include a process during which the PMMA surface is aminated. After this the microfluidic device can be biofunctionlizated by biotinilated antibodies. Two different protocols can be used to aminate the PMMA which are schematically represented in FIGS. 9A and 9B.

Figure 9:
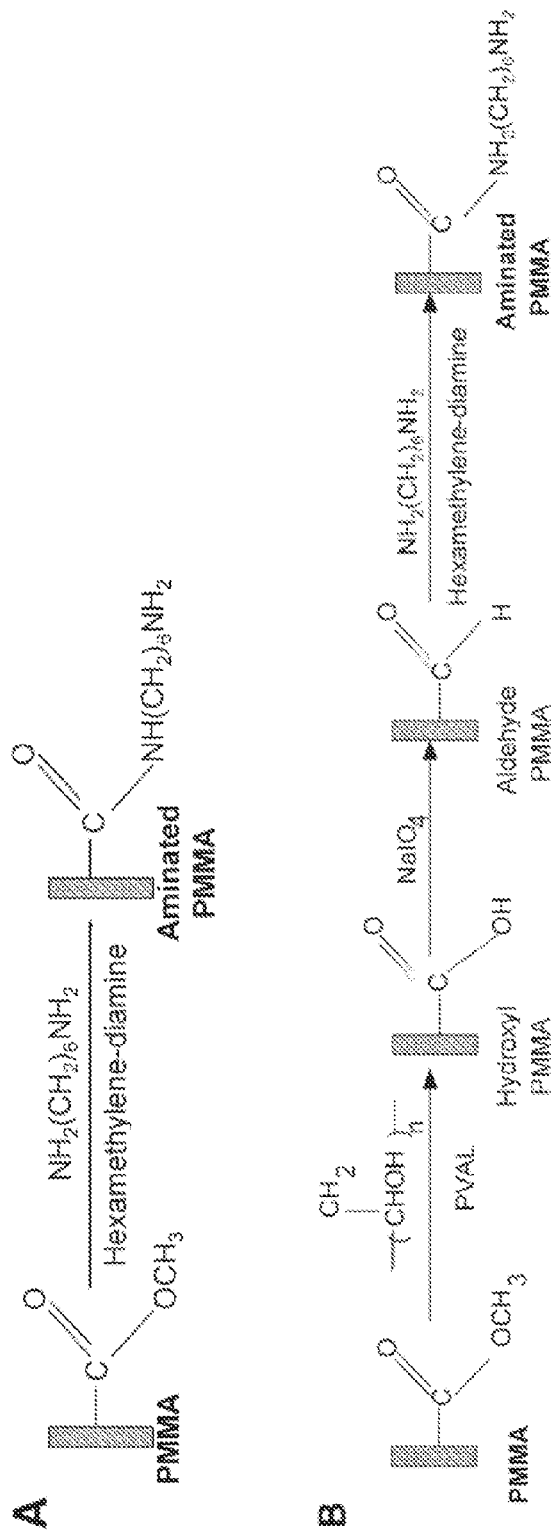
FIGS. 9A-B show schemes of the biofunctionalization protocol for aminating PMMA.
Figure 10:
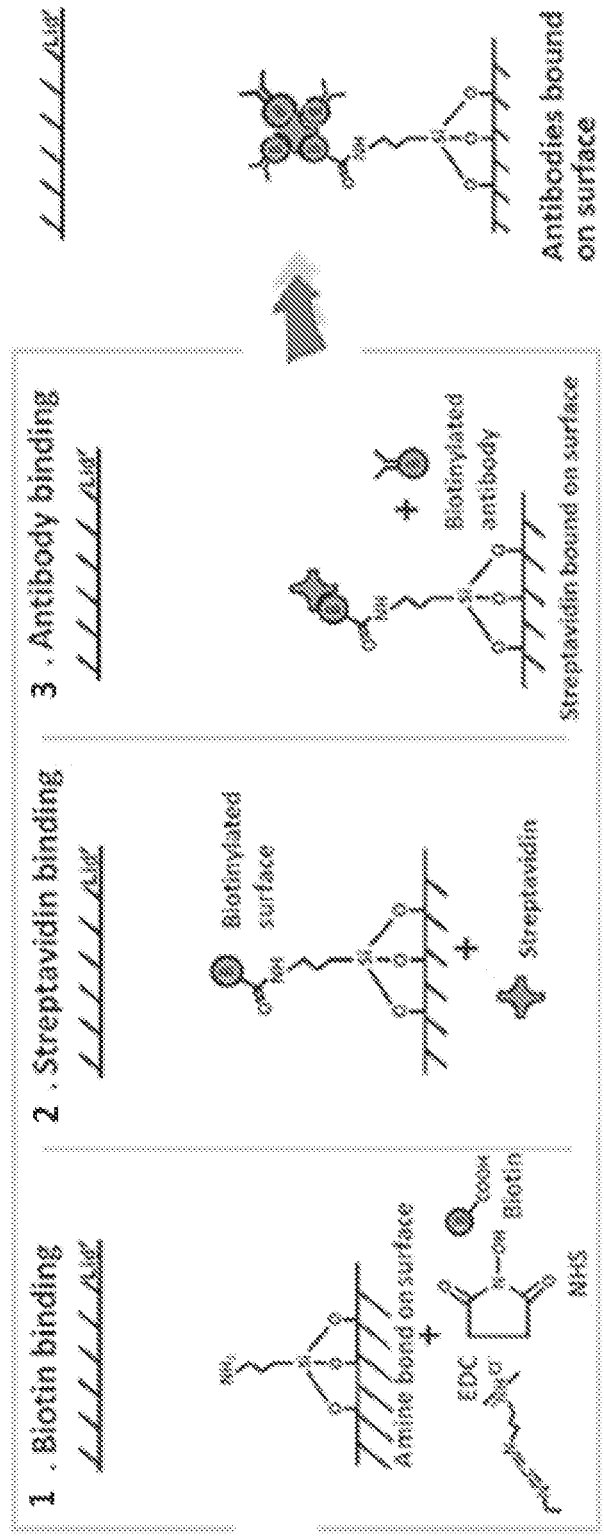
FIG. 10 is a schematics of the protocols of functionalization for covalently binding biotinylated antibodies on a surface of aminated PMMA.

In the first procedure of FIG. 9A, the PMMA is first washed by injecting inside it isopropanol (99%) at room temperature and then washed in DI water. Successively, 10% of "hexamethylene diamine" in 100 mM "borate buffer" pH 11.5, is injected in the device and incubated for two hours followed by DI water washing step of 10 minutes each. Finally the devices are left overnight at 30° C. to let them dry.

In the second procedure of FIG. 9B, the device is washed by injecting inside NaOH 10% (w/v) followed by ethanol 50% (v/v). Then a solution of 1 g/l di polyvinyl alcohol for 10 minutes is injected in the device, followed by a solution of 1% di NaIO4 for 1 hour at room temperature. Successively, 10% of "hexamethylene diamine" in 100 mM "borate buffer" pH 11.5 is injected and incubated for two hours. Finally the device is washed with a solution of "borate buffer" with pH 11.5 and 8.2, for 15 minutes each.

After the amination, the device is incubated with biotin (2 mg/ml), EDC (10 mg/ml) and NHS (15 mg/ml) in DI water for two hours at 4° C. Successively the streptavidin (2 mg/ml) in "phosphate buffer solution" (PBS), is immobilized on the biotinylated surface of the device by means of incubation in the upper chamber for 1 hour at 4° C. For this operation 1 mg of streptavidin in 500 µl of PBS and 1.63 µl of sodium azide is used. After this, the biotinylated antibody is prepared in a solution of PBS with 0.2 mg/ml of Tris with pH 7.3 containing 0.1% of albumin is incubated overnight. After each functionalization step, the device is washed with PBS. The following picture shows the schematic representation of the biofunctionlization process.

Working Principle of the Device

The device is able to handle biological samples containing cells of different species. It is possible to use also full blood or diluted or pretreated blood to deplete red blood cells from white blood cells and tumor cells. It is suggested to use anticoagulant in the blood to avoid cluster formations. The biological samples can be diluted in blood.

The device can be used by injecting a biological sample directly by using a pipette, or by connecting it to a syringe pump. The first method requires no external set-up but allow handling small volumes of samples (max 10 microliters). The second method requires an external set-up to manage the device but it allows handling bigger volume of samples up to 1 ml.

To handle bigger volumes it is possible to connect several devices in parallel.

The first protocol consists in filling the microfluidic device with the biological samples by using a pipette. The pipette is charged with the biological sample, it is connected to an inlet of the upper chamber of the device and the sample is injected in the microfluidic device. The following step is to wait for 10 seconds to allow the small cells and debris to go through the membrane by gravity. After 10 seconds the sample need to be sucked by the pipette and injected again alternatively for several times. This step allows shaking the sample in the device. Then, the cells are left again for 10 seconds to pass though the membrane by gravity. These operations should be repeated until the desired sample purity is not reached. The filtered samples can be then recovered from the upper chamber by flushing it with a syringe connected to it at high flow rate (in the range of 1 ml/min) and clogging the inlet and outlet of the bottom chamber.

Figure 11:
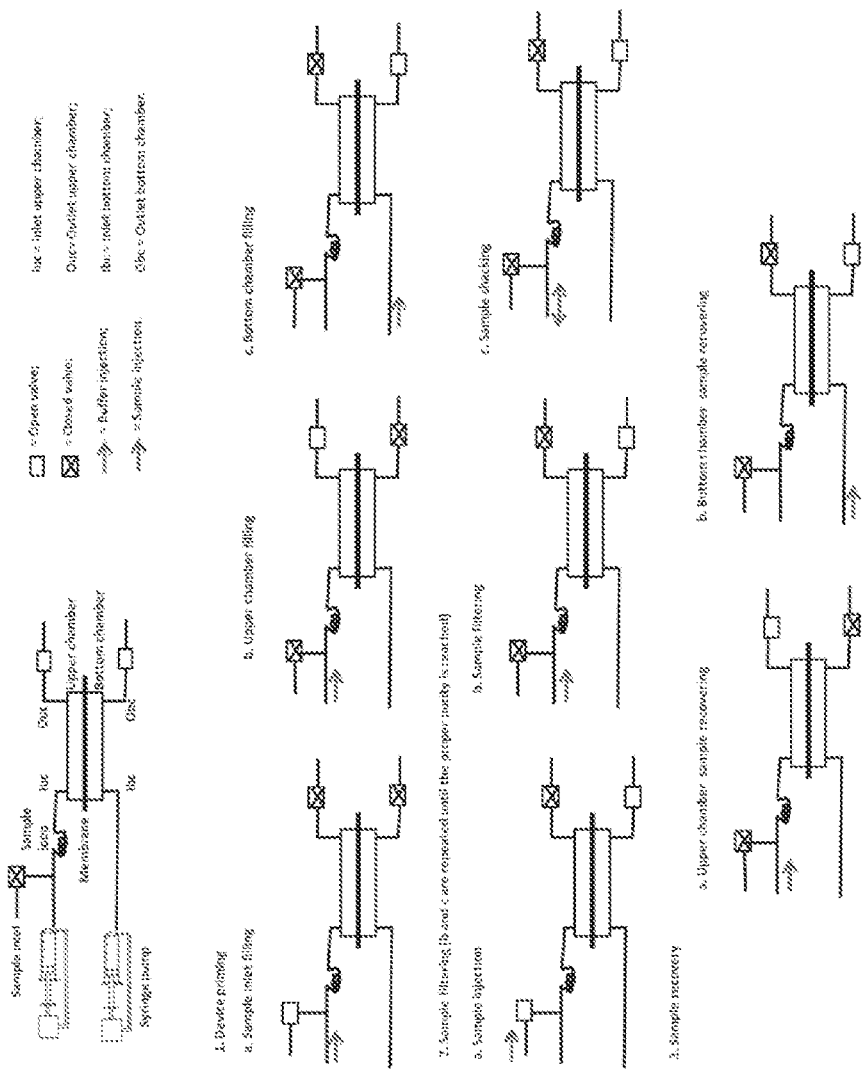
FIG. 11 shows schematic representation of the automated protocol to filter biological samples.

The second protocol can be used when the microfluidic device is connected to an external fluidic set-up and syringe pumps. The protocol can be described in the following steps:

1) The device is primed with buffer by filling the sample inlet (FIG. 11-1a: the valves in Ouc and Obc are closed, the valve in sample inlet is open), the upper chamber (FIG. 11-1b: the valves in Obc and sample inlet are closed, the valve in Ouc is open) and the bottom chamber (FIG. 11-1c: the valves in Ouc and sample inlet are closed, the valve in Obc is open) at a flow rate of 1 ml/min;

2) The biological sample is injected though the sample inlet port by using a syringe and pushing the sample slowly (FIG. 11-2a: the valves in sample inlet and Obc are open, the valve in Ouc is closed);

3) A volume of 1 microliter of buffer is injected pushing the biological sample from the upper chamber to the bottom chamber to filter the same sample at a flow rate of 1-10 µl/min (FIG. 11-2b: the valves in Ouc and sample inlet are closed, the valve in Obc is open);

4) A volume of 1 microliter of buffer is injected and withdrawn alternatively for 5-10 times at a flow rate of 100-1000 µl/min to shake the biological sample (FIG. 11-2c: the valves in Ouc and sample inlet are closed, the valve in Obc is open);

5) The operations 3 and 4 are repeated until the total volume of the biological sample is filtered;

6) The filtered sample in the upper chamber is recovered by flushing at a flow rate of 100-1000 µl/min 1 ml of buffer (FIG. 11-3a: the valves in Obc and sample inlet are closed, the valve in Ouc is open);

7) The filtered sample in the bottom chamber is recovered by flushing at a flow rate of 100-1000 µl/min 1 ml of buffer (FIG. 11-3c: the valves in Ouc and sample inlet are closed, the valve in Obc is open);

Using such protocols it is possible to get a purity of 95% using the manual protocol and 97% of purity by using the automated protocol. In fact, by using a sample constituted of 150.000 redblood cells/µl and 2.500 tumor cells/µl diluted in 0.5 ml of PBS, it was possible to deplete the above mentioned percentage of red blood cells from tumor cells.

Other embodiments are within the scope of the following claims.

What is claimed is:

1. A device for sorting cells comprising a microfluidic device including:
   a top layer including,
      a top inlet and a top outlet, said top inlet for introduction of a sample of cells and said top outlet for collection of cells retained in the top layer, said top layer includes at least one of poly(methyl methacrylate), polycarbonate, fluoropolymer, topas, silicone, polystyrene, or a combination thereof,
      a first chamber, and
      first and second top microfluid channels extending along the top layer, wherein the first top microfluid channel fluidly connects the top inlet to the first chamber and the second top microfluid channel fluidly connects the top outlet to the first chamber;
   a middle layer having a second chamber;
   a bottom layer including,
      a bottom inlet and a bottom outlet, said bottom inlet for introduction of a buffer solution and said bottom outlet for collection of cells retained in the bottom layer, said bottom layer includes at least one of poly(methyl methacrylate), polycarbonate, fluoropolymer, topas, silicone, polystyrene, or a combination thereof, and
      first and second bottom microfluid channels extending along the bottom layer, wherein the first bottom microfluid channel fluidly connects the bottom inlet to the second chamber and the second bottom microfluid channel fluidly connects the bottom outlet to the second chamber; and
   a membrane between the top layer and the middle layer, the membrane having a thickness between 2 and 100 micrometers, said membrane includes antibodies and at least one of poly(methyl methacrylate), polycarbonate, fluoropolymer, topas, silicone, polystyrene, or a combination thereof, wherein the membrane separates the first chamber from the second chamber, and wherein the membrane has a plurality of openings that allow cells to pass from the first chamber to the second chamber.

2. The device of claim 1, wherein the membrane is biofunctionalized with one or more biotinylated antibodies.

3. The device of claim 2, wherein the membrane is aminated prior to addition of the biotinylated antibodies.

4. The device of claim 1, wherein at least one of the top layer and the bottom layer is made of poly(methyl methacrylate).

5. The device of claim 1, wherein the membrane includes a plurality of rectangular openings.

6. The device of claim 1, wherein the membrane includes a plurality of circular openings.

7. The device of claim 1, wherein the membrane includes a plurality of cross-shaped openings.

8. The device of claim 1, wherein the membrane is poly(methyl methacrylate).

9. The device of claim 1, wherein the device has a thickness of between 0.2 to 2 millimeters.

10. The device of claim 1, wherein the cells include at least one of a tumor cell, a white blood cell, or a red blood cell.

11. A method of separating a plurality of categories of cells in a sample, the method comprising:

providing a microfluidic device having a top layer, a middle layer, a bottom layer, and a membrane, the top layer including, a top inlet and a top outlet, a first chamber, and first and second top microfluid channels, wherein the first top microfluid channel fluidly connects the top inlet to the first chamber and the second top microfluid channel fluidly connects the top outlet to the first chamber, the middle layer having a second chamber, the bottom layer including, a bottom inlet and a bottom outlet, first and second bottom microfluid channels, wherein the first bottom microfluid channel fluidly connects the bottom inlet to the second chamber and the second bottom microfluid channel fluidly connects the bottom outlet to the second chamber, and the membrane being located between the top layer and the middle layer, the membrane having a thickness between 2 and 100 micrometers, said membrane includes antibodies, a plurality of openings, and at least one of poly(methyl methacrylate), polycarbonate, fluoropolymer, topas, silicone, polystyrene, or a combination thereof; wherein said membrane separates the first chamber from the second chamber;

adding a sample including a plurality of categories of cells into the top inlet of said microfluidic device, passing some but not all of said cells through the membrane in the microfluidic device, said cells passing through the membrane based on size, shape or antibody specificity, and collecting two output streams from the top and bottom outlets of the microfluidic device, each output stream including cells of different categories, wherein at least one output stream contains cells passed through the membrane based on size, shape or antibody specificity, and at least one stream contains cells that did not pass through the membrane.

12. The method of claim 11, wherein adding cells includes injecting cells or pumping cells into the top inlet.

13. The method of claim 11, wherein the membrane is biofunctionalized with one or more biotinylated antibodies.

14. The method of claim 11, wherein at least one of the top layer and the bottom layer includes at least one of poly (methyl methacrylate), fluoropolymer, topas, silicone, polystyrene, or a combination thereof.

15. The method of claim 11, wherein the plurality of openings are rectangular shaped, circular shaped or cross-shaped.

16. A device for sorting cells comprising a microfluidic device including:

a top layer including a top inlet and a top outlet, a first chamber, and first and second top microfluid channels extending along the top layer, wherein the first top microfluid channel fluidly connects the top inlet to the first chamber and the second top microfluid channel fluidly connects the top outlet to the first chamber;

a middle layer having a second chamber;

a bottom layer including a bottom inlet and a bottom outlet, and first and second bottom microfluid channels extending along the bottom layer, wherein the first bottom microfluid channel fluidly connects the bottom inlet to the second chamber and the second bottom microfluid channel fluidly connects the bottom outlet to the second chamber; and a membrane between the top layer and the bottom layer, said membrane being biofunctionalized with one or more biotinylated antibodies, wherein the membrane separates the first chamber from the second chamber, and wherein the membrane has a plurality of openings that allow cells to pass from the first chamber to the second chamber.

17. The device of claim 16, wherein the membrane is aminated prior to addition of the biotinylated antibodies.

18. The device of claim 16, wherein the membrane is poly(methyl methacrylate).

19. The device of claim 16, wherein the device has a thickness of between 0.2 to 2 millimeters.

20. The device of claim 16, wherein the plurality of openings are rectangular openings, circular openings, cross-shaped openings, or triangular openings.

* * * * *